United States Patent
Heaney et al.

(10) Patent No.: US 7,503,105 B2
(45) Date of Patent: Mar. 17, 2009

(54) LOADING STENT WITH COMPRESSED AIR

(75) Inventors: Barry Heaney, Ballybrit (IE); Gabriel Sobrino Serrano, Kinvara (IE); Michael Austin, Newport (IE); John Motherwell, Kinvara (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 534 days.

(21) Appl. No.: 11/109,407

(22) Filed: Apr. 19, 2005

(65) Prior Publication Data

US 2006/0230592 A1  Oct. 19, 2006

(51) Int. Cl.
*B23P 11/02* (2006.01)

(52) U.S. Cl. .................................................. 29/508

(58) Field of Classification Search ............. 623/1.11; 221/304, 278; 29/225, 235, 270, 272, 282, 29/283.5, 508, 715
See application file for complete search history.

(56) References Cited

U.S. PATENT DOCUMENTS

| | | | | |
|---|---|---|---|---|
| 4,038,051 A * | 7/1977 | Ide | ............................. | 96/408 |
| 5,423,885 A * | 6/1995 | Williams | ............................. | 623/1.17 |
| 6,096,027 A * | 8/2000 | Layne | ............................. | 606/1 |
| 6,360,577 B2 * | 3/2002 | Austin | ............................. | 72/402 |
| 6,454,495 B1 * | 9/2002 | Meins | ............................. | 406/19 |
| 6,539,984 B2 * | 4/2003 | Lam | ............................. | 140/71 R |
| 6,568,235 B1 * | 5/2003 | Kokish | ............................. | 72/402 |
| 6,618,921 B1 | 9/2003 | Thornton | ............................. | 29/270 |
| 6,629,350 B2 * | 10/2003 | Motsenbocker | ............................. | 29/283.5 |
| 6,863,683 B2 | 3/2005 | Schwager et al. | ............................. | 623/1.11 |
| 7,316,147 B2 * | 1/2008 | Perreault et al. | ............................. | 72/402 |
| 2001/0001890 A1 | 5/2001 | Austin | ............................. | 29/282 |
| 2004/0148007 A1 | 7/2004 | Jackson et al. | ............................. | 623/1.12 |
| 2004/0199239 A1 | 10/2004 | Austin et al. | ............................. | 623/1.11 |
| 2005/0166389 A1 | 8/2005 | Perreault et al. | ............................. | 29/508 |
| 2005/0183259 A1 | 8/2005 | Eidenschink et al. | ............................. | 29/508 |
| 2005/0188525 A1 | 9/2005 | Weber et al. | ............................. | 29/508 |

FOREIGN PATENT DOCUMENTS

WO  WO 2005/082578  9/2005

OTHER PUBLICATIONS

U.S. Appl. No. 10/755,752, filed Jan. 12, 2004, Larson et al.

* cited by examiner

*Primary Examiner*—(Jackie) Tan-Uyen T. Ho
*Assistant Examiner*—Gregory A Anderson
(74) *Attorney, Agent, or Firm*—Vidas, Arrett & Steinkraus, P.A.

(57) ABSTRACT

A stent loading system comprises a contracting aperture device having blades defining a contracting aperture and a fluid supply source. The blades are movable so as to vary the size of the contracting aperture. A stream of fluid is supplied by a fluid supply source and enters the contracting aperture and travels longitudinally through the contracting aperture. The stream of fluid is arranged to transport a stent from the contracting aperture contracting aperture and outside the contracting aperture device.

23 Claims, 6 Drawing Sheets

LOADING STENT WITH COMPRESSED AIR

BACKGROUND OF THE INVENTION

A stent is typically a tubular member that is placed in a lumen in the body. The term "stent" throughout this disclosure includes, but is not limited to, stents and covered stents, 'stent-grafts' and other expandable, tubular frameworks.

Stents can be delivered inside a body lumen or vessel in a compacted or reduced-size form by a catheter. Upon reaching the site, the stent is expanded, for example, so that it can contact the walls of the lumen.

In some cases, the stent is formed of a material that can be reversibly compacted and expanded, e.g., elastically, through balloon expansion, or through a material phase transition. During introduction into the body, the stent is restrained in a compacted condition. Upon reaching the desired implantation site, the restraint is removed, for example, by retracting a restraining device such as an outer sheath, enabling the stent to self expand by its own internal restoring force.

In some instances the stent is crimped for catheter delivery. During crimping and placement on the catheter the stent can be damaged. The surface of the stent can be damaged or coatings can be damaged or scraped off.

There yet remains a need for a loading system which reduces contact between the stent and the equipment used in loading the endoprosthesis thereby reducing the risk of a stent coating being abraded and scraped which might lead to the production of embolic particles subsequently being deployed with the stent.

All US patents and applications and all other published documents mentioned anywhere in this disclosure are incorporated herein by reference in their entirety.

Without limiting the scope of the invention a brief summary of the claimed embodiments of the invention is set forth below. Additional details of the summarized embodiments of the invention and/or additional embodiments of the invention can be found in the Detailed Description of the Invention below.

A brief abstract of the technical disclosure in the specification is provided as well for the purposes of complying with 37 C.F.R. 1.72.

SUMMARY OF THE INVENTION

In at least one embodiment, a stent loading system comprises a contracting aperture device having blades defining a contracting aperture and a fluid supply source supplying a stream of fluid arranged to transport a stent longitudinally through the length of the aperture and outside the contracting aperture device. In at least one embodiment, the blades can be movable so as to vary the size of the contracting aperture. In at least one embodiment, a catheter is engaged to the contracting aperture device. In at least one embodiment, the contracting aperture and a lumen within the catheter can be in communication and can comprise a common device flow lumen. In at least one embodiment, a stream of fluid can be supplied by the fluid supply source and enter the device flow lumen. The stream of fluid can transport a stent from the contracting aperture into the catheter lumen through the device flow lumen.

In at least one embodiment the contracting aperture device is a contracting iris device.

In at least one embodiment, the system includes a chilling system that can chill the quantity of fluid. In at least one embodiment, the stream of fluid can be chilled and controllably released through the chilling system and into the device flow lumen.

In at least one embodiment, the stent loading system includes a fluid accumulator which can accumulate a quantity of fluid from the fluid supply source before releasing the fluid into the device flow lumen.

In at least one embodiment, the stent loading system comprises a valve. In at least one embodiment, the valve can govern the amount and duration of the fluid released from the accumulator into the device flow lumen.

In at least one embodiment, a single stream or multiple streams of chilled fluid can transport a stent with a diameter smaller than that of the aperture from the aperture into the guide housing.

In at least one embodiment, the system can further comprise a catheter having a first end within the guide housing. In at least one embodiment, the system can be constructed and arranged such that a stent entering the guide housing is also disposed within the catheter.

In at least one embodiment, the stent can have a crimped state and an uncrimped state.

In at least one embodiment, the device can have a widened position and a constricted position such that when in the widened position the aperture has a diameter in cross-section larger than that of the diameter of the aperture in the constricted position.

In at least one embodiment, a non-contaminating barrier can be disposed within the aperture of the contracting aperture device and the aperture of the guide housing. In at least one embodiment, the non-contaminating barrier can be a polymer sleeve, tube, or sock. In at least one embodiment, the non-contaminating barrier separates the contracting aperture device and the catheter aperture of the guide housing from a stent placed within the system. In embodiment where the stent comprises a therapeutic agent, the barrier substantially prevents a therapeutic agent or other residuals from a stent previously loaded from remaining within the aperture during the loading of another stent. In at least one embodiment, the non-contaminating barrier can be disposable and replaceable.

In at least one embodiment, the system can further comprise a fluid nozzle. In at least one embodiment, the stream of fluid can pass through the nozzle before entering the device flow lumen.

In at least one embodiment, the blades can be constructed and arranged to linearly slide.

In at least one embodiment, the blades can be constructed and arranged to pivot in order to vary the size of the aperture.

In at least one embodiment, a programmable controller and stepping motor can be used to vary the size of the aperture.

In at least one embodiment, the chilling system can reduce the temperature of the fluid to within about the range −5 C to −90 C. In at least one embodiment the chilling system can reduce the temperature of the fluid to a temperature that ensures that self expanding shape-memory stent alloys transform completely to a Martensitic phase.

In at least one embodiment, a control mandrel can be inserted into the catheter. In at least one embodiment, the mandrel can prevent a stent from traveling beyond a desired depth within the catheter.

In at least one embodiment, the stent can be comprised of a self-expanding material. In at least one embodiment, the stent can include a therapeutic agent.

In at least one embodiment, the system can further comprise a compressed fluid supply. In at least one embodiment, the fluid supply can communicate with a solenoid valve which is capable of governing the release of multiple streams of fluid into the device flow lumen. The solenoid valve can be pneumatic or electric.

In at least one embodiment, the system can further comprise a fluid accumulator. In at least one embodiment, the system can further comprise an accumulator pressurizing pump. In at least one embodiment, the accumulator pressurizing pump can further pressurize and pump the fluid from the fluid supply into the fluid accumulator. In at least one embodiment, the fluid accumulator can be in communication with the solenoid valve which governs the release of fluid from the fluid accumulator into the device flow lumen.

In at least one embodiment, the system can further comprise a fluid dryer disposed between the compressed fluid supply and the solenoid valve. In at least one embodiment, the fluid dryer can dry the fluid from the compressed fluid supply before release into the aperture.

In at least one embodiment, the sleeve, when in an uninflated condition, can be capable of folding and/or entering into gaps situated between the blades.

In at least one embodiment, the system can have a refrigerating chamber which chills the fluid within the fluid accumulator.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described various embodiments of the invention.

DETAILED DESCRIPTION OF THE INVENTION

Figure 1:
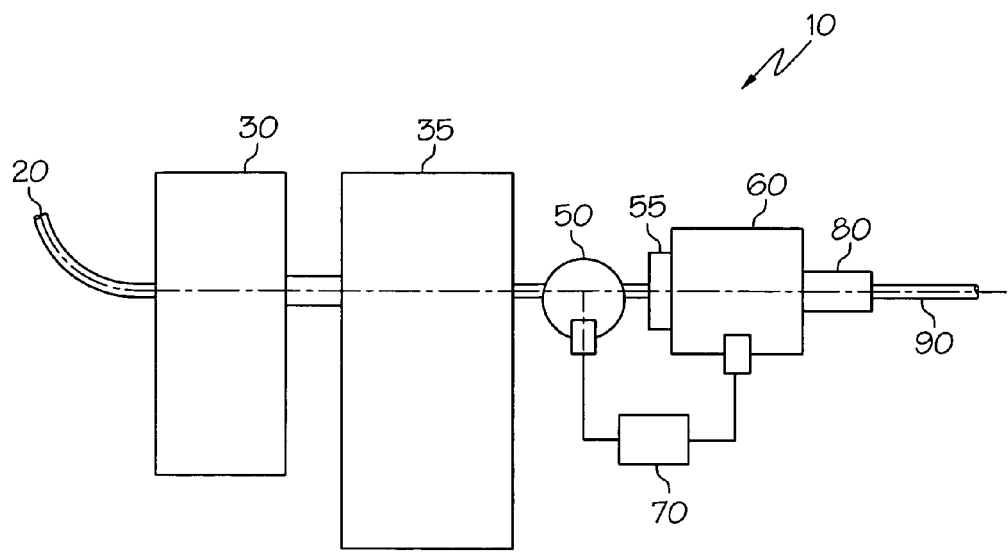
FIG. 1 is a flat view schematic of a fluid jet stent loading system.

While this invention can be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Also for the purposes of this disclosure, the term 'stent' refers to an expandable prosthesis for implantation into a body lumen or vessel and includes devices such as stents, grafts, stent-grafts, vena cava filters, tubular expandable frameworks (regardless of whether they can support a vessel), etc. In addition, for purposes of this disclosure the term "fluid" refers to gases or liquids and the term "air" refers to any gas including gas mixtures; if "air" is used specifically rather than "fluid", it should be understood that the invention also contemplates the use of any fluid in place of the air. Furthermore, for purposes of this disclosure the term "stream" (with regards to fluid) refers to any puff, jet, or movement of fluid. Finally, for purposes of this disclosure, the term "crimped" in reference to a stent is a reduction in the diameter of the stent.

Referring to FIG. 1, a schematic of a fluid jet stent loading system 10 is illustrated. In this illustration a compressed air/gas supply 20 is attached to a fluid dryer 30 which dries the gas before being transferred into a gas chiller 35. The fluid within the gas chiller 35 can be chilled to between about −5 C to −90 C. In some instances it is chilled to between about −5 C to −50 C.

A solenoid valve 50 regulates the release of the fluid from the compressed air supply through the nozzle housing 55 and into the aperture of the contracting aperture device 60. The nozzle housing 55 includes a nozzle which can control the direction of and increase the velocity of the released air. The fluid can be released in multiple streams or in a single jet stream. The solenoid valve can be a pneumatic solenoid valve controlled by a microprocessor controller 70. The microprocessor controller 70 can also control the widening and constricting of the aperture of the contracting aperture device 60. The aperture device 60 is in fluid communication with delivery sheath location and guide housing 80. A delivery catheter 90 can also reside within the housing 80. It should be noted that in some embodiments the guide housing is not included and the catheter may engage the contracting aperture device without the guide housing.

Figure 2:
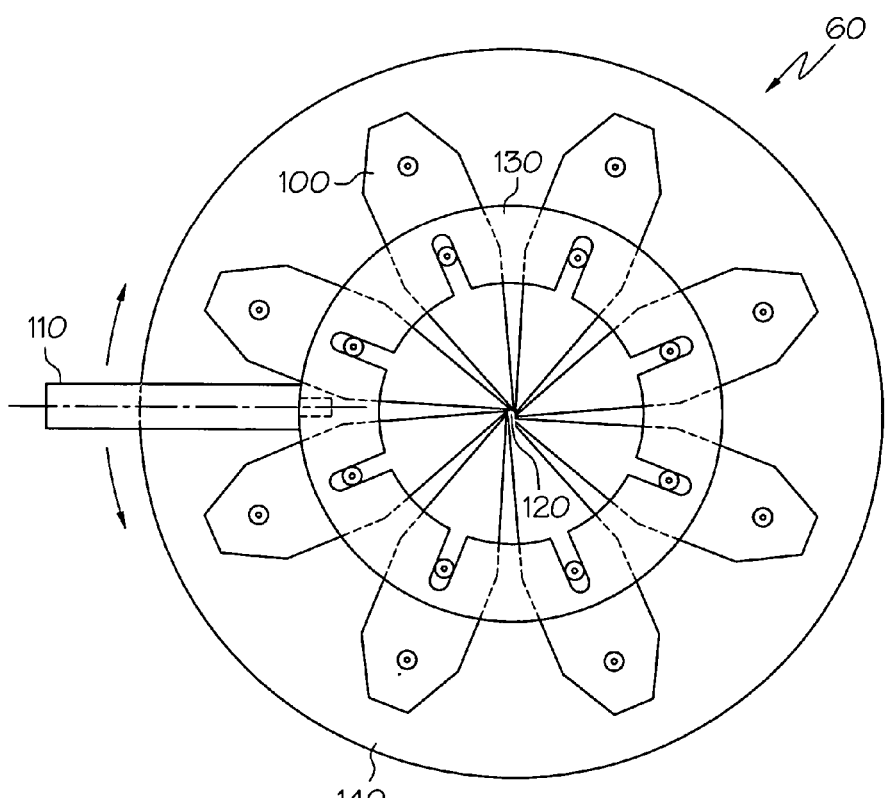
FIG. 2 is an end view of a stent contracting aperture device.

In FIG. 2 an end view of a stent contracting aperture device is illustrated. In some embodiments the stent contracting aperture device can be a contracting iris. In FIG. 2 blades 100 pivot upon actuation of a rotary actuator 110. The pivoting of the blades 100 results in an increase or decrease in the diameter of the aperture 120. Rotary actuator 110 rotates the aperture actuation ring 130 in relation to blade pivot mounting plate 140. It should be noted that FIG. 2 represents only an example of a stent contracting mechanism or contracting aperture device. In some embodiments of the present invention, the contracting device 60 utilize blades constructed and arranged to linearly slide rather than strictly pivot.

Figure 3:
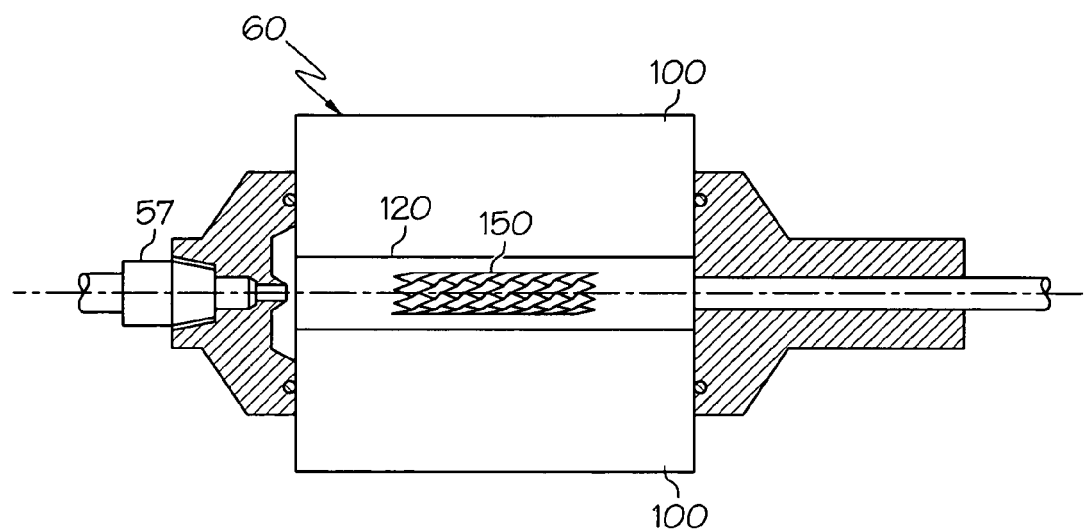
FIG. 3 is a cross-sectional view of a contracting aperture device in a widened position.

FIG. 3 is a cross-sectional view of a contracting aperture device 60 in a widened position. In this illustration the stent 150 resides in the aperture 120 before the aperture has been constricted and the stent crimped.

Figure 4:
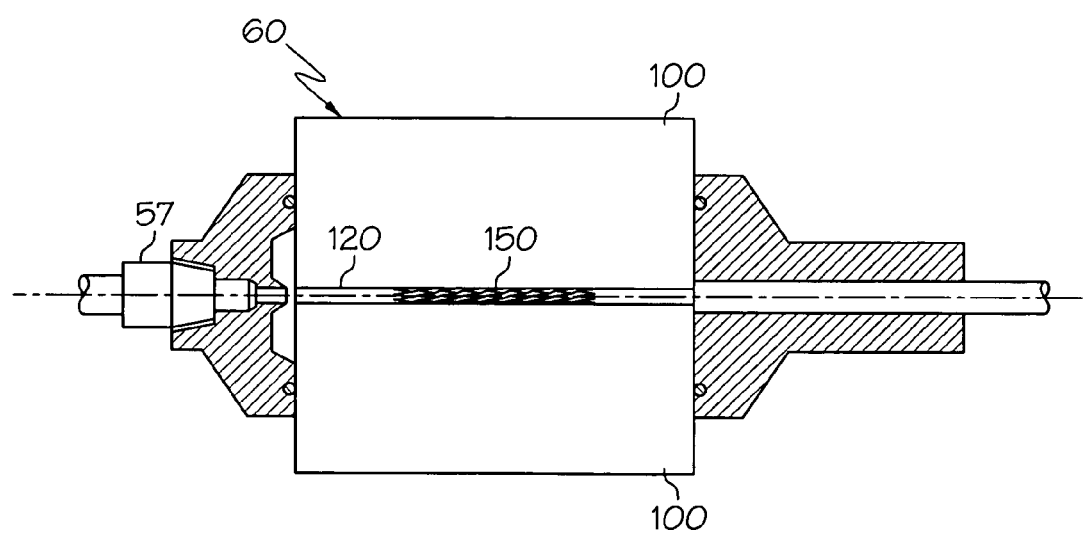
FIG. 4 is a cross-sectional view of a contracting aperture device in a constricted position.

FIG. 4 is a cross-sectional view of a contracting aperture device 60 in a constricted position. In this illustration, the stent 150 has been crimped to a smaller diameter. It should be noted that the blades 100 and the stent 150 can be reduced in temperature by the chilled fluid which is typically in the range of about −5 C to −90 C. The chilled fluid serves more purposes than transport. By chilling the blades 100 and stent 150 before the stent 150 is crimped the alloy of the stent is transformed into its martensitic phase and reduces the amount of force necessary in crimping the stent. This chilling can also inhibit recovery of memory to the original non-crimped diameter thus providing for freer passage of the crimped stent in the loading gas stream. In addition any polymer coating on the stent is hardened thereby making the coating more resistant to surface deformations. Furthermore, the chilled fluid also reduces the temperature of the delivery sheath of catheter 90 over a sufficient length to inhibit the expansion of the stent until it reaches its fully loaded depth (shown in FIG. 6).

Figure 5:
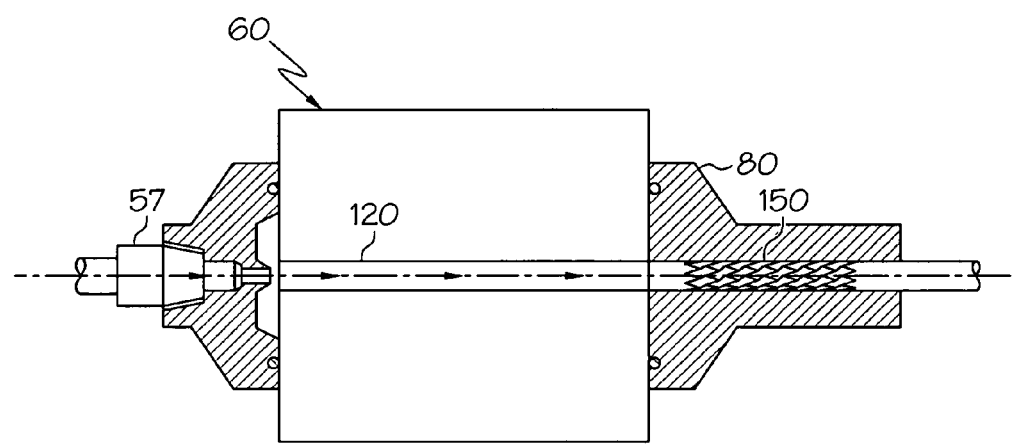
FIG. 5 is a cross-sectional view of a contracting aperture device and guide housing with a stent loaded in the delivery catheter.

In FIG. 5 a cross-sectional view of a contracting aperture device and guide housing is shown after the stent 150 has been crimped as in FIG. 4. The contracting aperture device 60 can include a programmable controller with an associated stepping motor. The stepping motor can open or close the aperture 120 of the contracting aperture device by very small discrete increments. FIG. 5 illustrates the aperture 120 after it has been opened to a wider diameter than that of the diameter in the constricted position. This provides clearance, as better illustrated in FIG. 8a, for the stent to be advanced from the contracting aperture device 60 of FIG. 5 into the housing 80 by force of released fluid through fluid nozzle 57. In some instances this clearance is between about 0.1 to 0.2 mm, though it can be less or more.

Figure 5A:
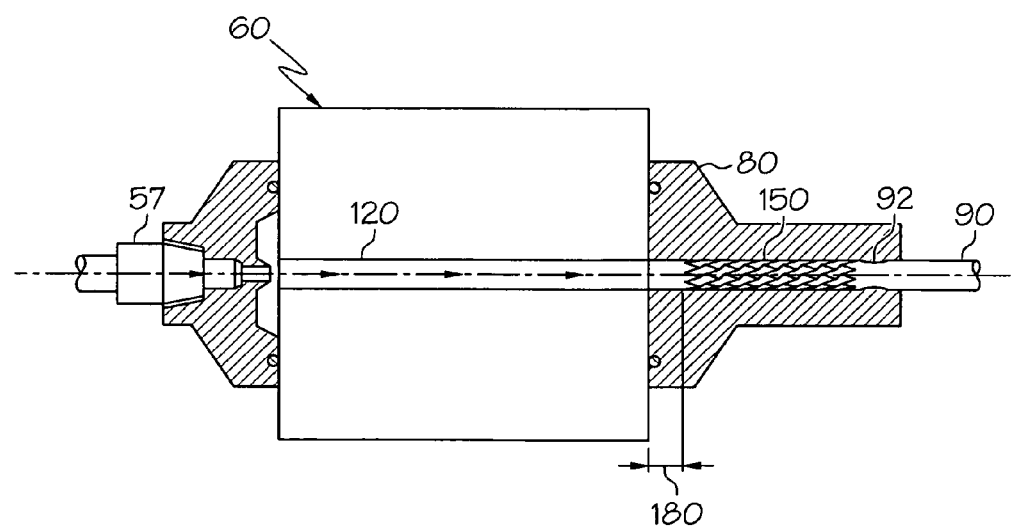
FIG. 5a is a cross-sectional view of a contracting aperture device and guide housing with a stent loaded in the delivery catheter.

In FIG. 5a the stent 150 is loaded within the catheter 90 within housing 80. A pinched portion 92 in delivery catheter 90 stops the travel of the stent 150 at a designated depth 180 within catheter 90.

Figure 6:
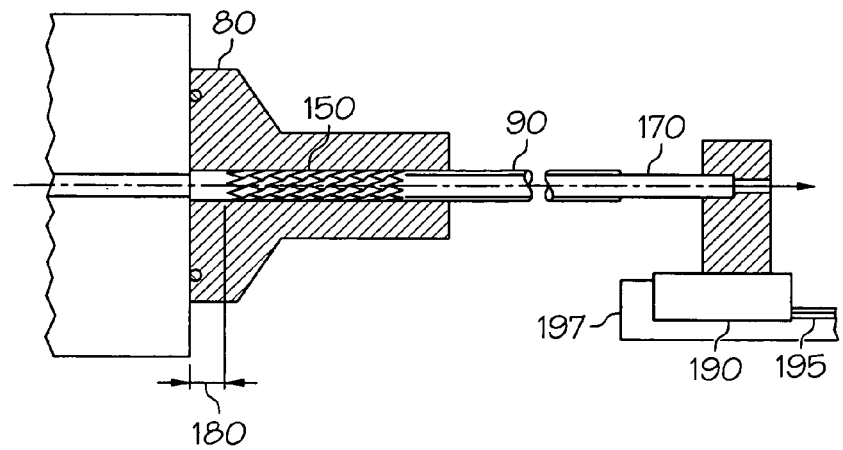
FIG. 6 is a cross-sectional view of a guide housing with a loaded stent and a loading depth control mandrel.

In FIG. 6 the stent 150 is loaded within the catheter 90 within housing 80. A mandrel or hypotube 170 is inserted into the delivery catheter 90 to a point, typically within the housing 80, which stops the travel of the stent 150 at a designated depth 180 within catheter 90. The mandrel 170 can be hollow to allow fluid to exhaust through it. In addition, the depth adjusting device 190 controls the position of the mandrel 170 within the catheter 90. The adjusting device 190 can be mounted on a linear bearing 195 which provides lateral movement up to the stop 197.

Figure 7:
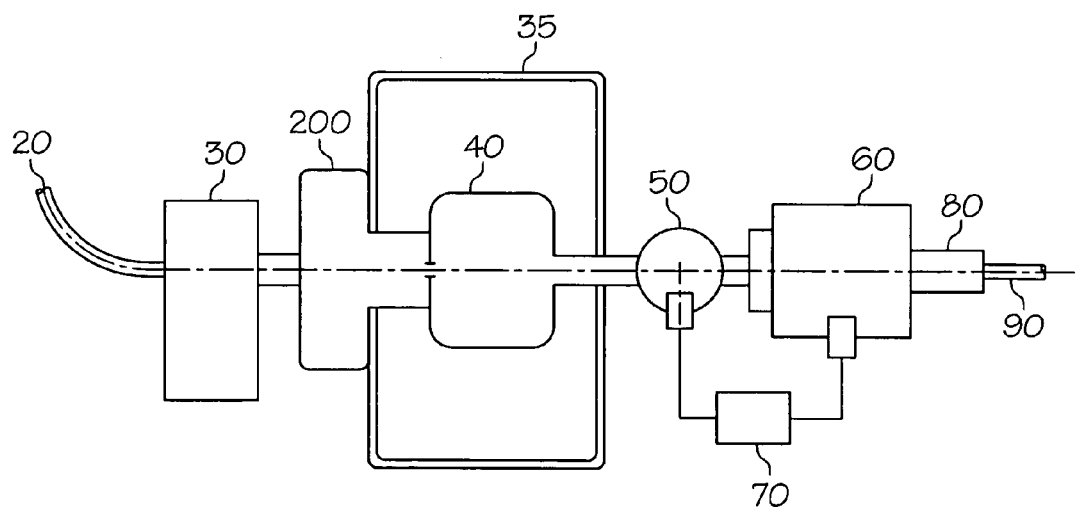
FIG. 7 is a flat view schematic of a fluid jet stent loading system with integral refrigeration accumulator.

FIG. 7 is a flat view schematic of a fluid jet stent loading system with an integral refrigeration accumulator. Air from the air supply 20 can be dried in the air dryer 30. From there the air may directly flow into an air accumulator 40 within chilling unit 35. Here the fluid is chilled in the accumulator 40. The accumulator 40 provides for a steadier release of air to the solenoid 50. In some embodiments, as shown, an accumulator pressurizing pump 200 can also be used to increase the pressure within the accumulator 40.

Figure 8:
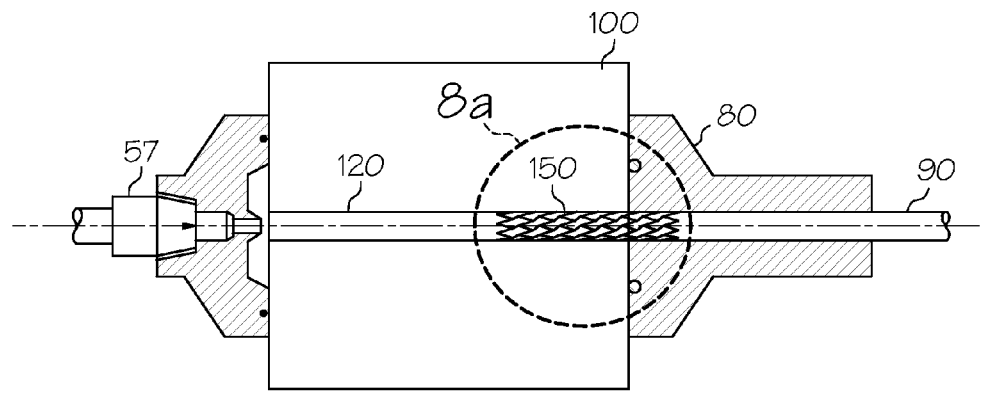
FIG. 8 is a cross-sectional view of a contracting aperture device with a partially loaded stent.

In FIG. 8 a cross-section of a contracting aperture device with a partially loaded stent is illustrated. Here, the stent 150 can be moving within the aperture 120 and catheter 90 on a stream of fluid or the stent can be momentarily stopped or almost stopped between multiple releases of air. The stent is still in a crimped position and the aperture 120 has opened enough for the release(s) of fluid from the nozzle 57 to advance the stent.

Figure 8A:
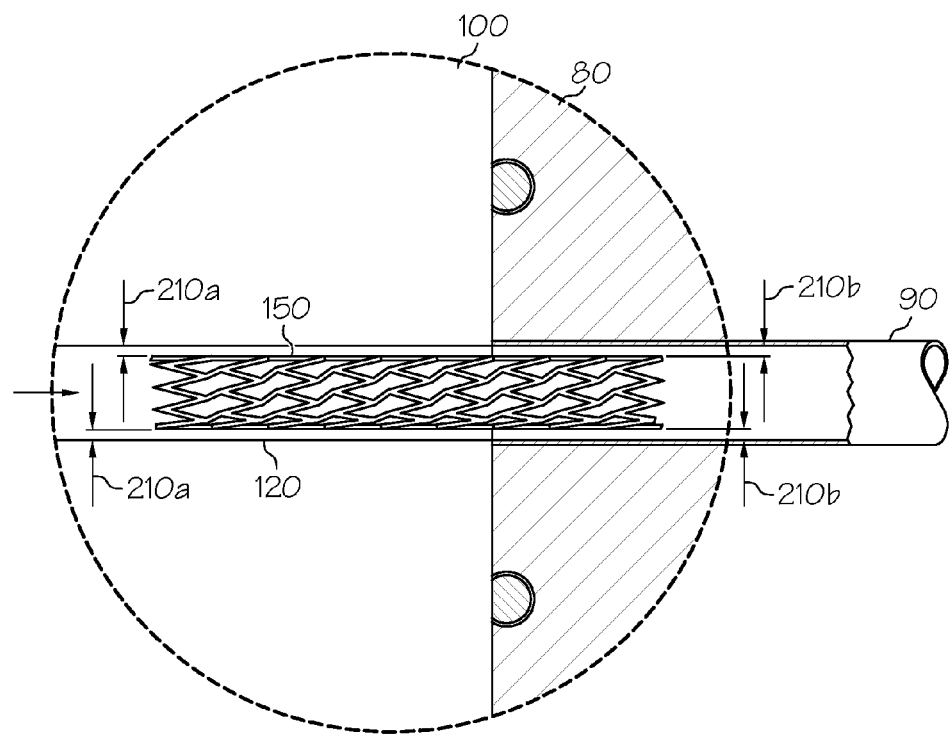
FIG. 8a is a cross-sectional view of an enlarged detail showing a partially loaded stent.

In FIG. 8a an enlarged detail showing a partially loaded stent 150. FIG. 8a illustrates the aperture clearance 210a that exists between the blades 100 about aperture 120 and the outside of the stent and the catheter clearance 210b that exists between the interior diameter of the catheter 90 and the outside of the stent 150. The aperture clearance is the difference in the diameter of the crimped and chilled stent 150 and the diameter of the opening of the aperture 120; and the catheter clearance is the difference in the diameter of the crimped and chilled stent 150 and the interior diameter of the catheter 90. The catheter clearance 210b is typically in the range of about 0.1 to 0.3 mm and is typically larger than the aperture clearance 210a.

Figure 9:
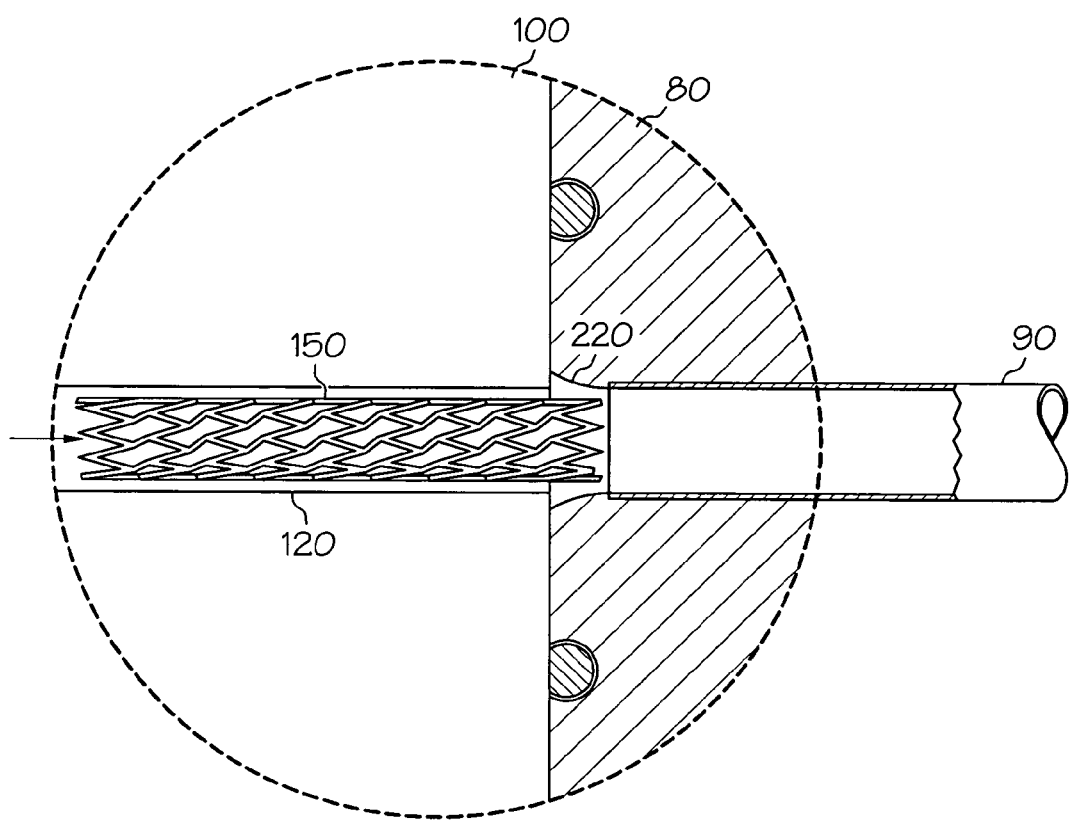
FIG. 9 is a cross-sectional enlarged view of a stent passing out of the contracting aperture device.

In at least one embodiment, as shown in FIG. 9, the housing 80 includes a conical portion 220 which is aligned with the aperture 120. The conical portion 220 acts as a lead to facilitate smooth loading. The catheter 90 contacts the conical portion 220. In some instances the conical portion 220 is a portion of or is temporarily attached to the catheter 90 which is then inserted into the housing 80 for loading of the stent 150.

Other embodiments of the invention are listed below:

A stent loading system comprising a contracting aperture device, a chilling system, and a guide housing; the contracting aperture device having blades defining an aperture, the blades being movable so as to vary the size of the aperture; the chilling system for chilling a quantity of air, the chilling system having a chilled fluid release nozzle capable of releasing at least one stream of chilled gas; a guide housing having an aperture; the chilled fluid release nozzle, the contracting aperture device, and delivery sheath location and guide housing being in fluid communication, the at least one stream of chilled gas capable of transporting a stent with a diameter smaller than that of the aperture from the aperture into the guide housing.

The system of the paragraph above wherein the blades are constructed and arranged to linearly slide.

The system of any of the paragraphs above wherein the aperture is defined by an iris mechanism.

The system of any of the paragraphs above wherein the contracting aperture device and the housing have a sealed interface.

The system of any of the paragraphs above wherein a stent as long as about 150 mm can be loaded. Such a system wherein the stent is longer than 150 mm.

The system of any of the paragraphs above wherein a coating on a stent being loaded experiences minimal with any part of the contracting aperture device or the guide housing.

The system of any of the paragraphs above wherein the blades are actuated by a rotary actuator and precision pneumatic or by an electronic linear actuator coupled to a radial actuation arm.

The system of any of the paragraphs above having a catheter engaged to the contracting aperture device. The system of any of the paragraphs above wherein a catheter is disposed within the guide housing and engaged to the contracting aperture device.

A stent loading system comprising a contracting aperture device, an accumulator, and a guide housing; the contracting aperture device having blades defining an aperture, the blades being movable so as to vary the size of the aperture; the accumulator releasing at least one stream of air; a guide housing having an aperture; the contracting aperture device, and delivery sheath location and guide housing being in fluid communication, the at least one stream of fluid capable of transporting a stent with a diameter smaller than that of the aperture from the aperture into the guide housing.

The system of any of the paragraphs above wherein fluid from the accumulator passes through a fluid nozzle before entering the contracting aperture.

The system of any of the paragraphs above having a non-contaminating barrier separating a stent from the aperture, the barrier using a roll-on/roll-off double spool.

The system of any of the paragraphs above having a non-contaminating barrier; the non-contaminating barrier is disposable and replaceable.

The system of any of the paragraphs above having a mandrel within the catheter which prevents the stent from entering the catheter beyond a prescribed depth; the mandrel position controlled by a depth adjusting device.

The system of any of the paragraphs above wherein the fluid in the fluid accumulator is released very precisely by a microprocessor controlled pneumatic solenoid valve.

The system of the above paragraph wherein the fluid is released such that one release of fluid transports a stent to its fully loaded position.

The system of any of the paragraphs above wherein the delivery catheter has a pinched portion which prevents the transport of a stent beyond the pinched portion.

The system of any of the paragraphs above wherein means for cleaning any residue or particulate matter from a previous stent loading can be cleaned from the aperture.

The system of any of the paragraphs above wherein a solvent-saturated mop or sponge-head is inserted into the aperture to remove particulate matter from the inner surface of the aperture.

The system of any of the paragraphs above wherein the fluid in the fluid accumulator is released very precisely by a microprocessor-controlled micro-pulse gas jets including linear positioning sensing of stent depth in the catheter.

The system of the paragraph above wherein the micro-pulse gas jets are capable of moving the stent in short steps such that just as the stent is almost stopped another gas pulse moves it further on until the stent is fully loaded.

A process using the system of any of the paragraphs above wherein a mandrel concentric with the aperture is inserted through the stent; the stent being crimped to a size slightly larger than the mandrel; the mandrel then removed and the stent is further crimped to its final size.

The system of any of the paragraphs above including a stent having a therapeutic agent. A therapeutic agent can be a drug or other pharmaceutical product such as non-genetic agents, genetic agents, cellular material, etc. The therapeutic agent can be a coating or contained within the structure of the stent. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent can include but is not limited to: DNA, RNA and their respective derivatives and/or components; hedgehog proteins, etc. Where a therapeutic agent includes cellular material, the cellular material can include but is not limited to: cells of human origin and/or non-human origin as well as their respective components and/or derivatives thereof. Where the therapeutic agent includes a polymer agent, the polymer agent can be a polystyrene-polyisobutylene-polystyrene triblock copolymer (SIBS), polyethylene oxide, silicone rubber and/or any other suitable substrate.

Stents can find use in coronary arteries, renal arteries, peripheral arteries including illiac arteries, arteries of the neck and cerebral arteries. The stents and, more generally, stents of the present invention, however, are not limited to use in the vascular system and can also be advantageously employed in other body structures, including but not limited to arteries, veins, biliary ducts, urethras, fallopian tubes, bronchial tubes, the trachea, the esophagus and the prostate.

The stents disclosed herein as well as those now known and those later developed can be at least partially constructed of any of a variety of materials such as stainless steel, nickel, titanium, nitinol, platinum, gold, chrome, cobalt, as well as any other metals and their combinations or alloys. In some embodiments, the stent can be at least partially constructed of a polymer material. In some embodiments, the stent can be at least partially constructed of a shape-memory polymer or material. In some embodiments, the stent can be balloon expandable, self-expandable, hybrid expandable or a combination thereof. In some embodiments, the stent can include one or more radiopaque members. In some embodiments, the stent can include one or more therapeutic and/or lubricious coatings applied thereto. In another embodiment the invention is also directed to the expandable framework geometries shown herein.

The above disclosure is intended to be illustrative and not exhaustive. This description will suggest many variations and alternatives to one of ordinary skill in this art. The various elements shown in the individual figures and described above can be combined or modified for combination as desired. All these alternatives and variations are intended to be included within the scope of the claims where the term "comprising" means "including, but not limited to". Those familiar with the art can recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

The description above describes several embodiments of the invention. Those skilled in the art can recognize other equivalents to the specific embodiment described herein which equivalents are intended to be encompassed by the claims attached hereto.

What is claimed is:

1. A stent loading system comprising:
    a contracting aperture device having blades defining a contracting aperture, the blades being movable so as to vary the size of the contracting aperture;
    a non-contaminating barrier disposed within the contracting aperture of the contracting aperture device, the non-contaminating barrier separating the contracting aperture device from a stent placed within the system;
    a fluid supply source, a stream of fluid supplied by the fluid supply source and entering the contracting aperture traveling longitudinally through the length of the aperture; and
    a chilling system for chilling the stream of fluid, the stream of fluid being chilled and controllably released through the chilling system and into the contracting aperture;
    wherein the chilled stream of fluid is arranged to transport a stent through the contracting aperture and outside the contracting aperture device.

2. The stent loading system of claim 1 further comprising a catheter engaged to the contracting aperture device and having a catheter lumen; the catheter lumen and contracting aperture being in communication with one another and comprising a device flow lumen such that the stream of fluid is arranged to transport a stent through the contracting aperture and into the catheter lumen of the catheter.

3. The stent loading system of claim 1 wherein the chilled stream of fluid transforms at least a portion of a self-expanding stent to a martinsitic phase and hardens a coating on the stent.

4. The stent loading system of claim 1 further comprising a valve, the valve governing the amount and duration of the fluid released through the valve and into the contracting aperture of the contracting aperture device.

5. The stent loading system of claim 1 further comprising a guide housing, the guide housing having a catheter aperture and constructed and arranged to engage a catheter therein, the guide housing attached to the contracting aperture device.

6. The stent loading system of claim 1 having a fluid accumulator for accumulating a quantity of fluid from the fluid supply source before releasing the fluid into the device flow lumen.

7. The stent loading system of claim 1 comprising a stent, the stent having a crimped state and an uncrimped state.

8. The stent loading system of claim 1 wherein the device has a widened position and a constricted position, when in the widened position the contracting aperture has a diameter in cross-section larger than that of the diameter of the contracting aperture in the constricted position.

9. The stent loading system of claim 1 further comprising a fluid nozzle, the stream of fluid passing through the nozzle before entering the contracting aperture.

10. The stent loading system of claim 1 wherein the blades are constructed and arranged to pivot in order to vary the size of the contracting aperture.

11. A stent loading system comprising:
   a contracting aperture device having blades defining a contracting aperture, the blades being movable so as to vary the size of the contracting aperture;
   a programmable controller and stepping motor used to vary the size of the contracting aperture;
   a fluid supply source, a stream of fluid supplied by the fluid supply source and entering the contracting aperture traveling longitudinally through the length of the aperture; and
   a chilling system for chilling the stream of fluid, the stream of fluid being chilled and controllably released through the chilling system and into the contracting aperture;
   wherein the chilled stream of fluid is arranged to transport a stent through the contracting aperture and outside the contracting aperture device.

12. The stent loading system of claim 1 wherein the chilling system reduces the temperature of the fluid to within about the range −5 C to −90 C.

13. The stent loading system of claim 6 comprising a control mandrel inserted into a catheter and constructed and arranged to prevent a stent from traveling beyond a desired depth within the catheter.

14. The stent loading system of claim 7 wherein the stent is comprised of a self-expanding material.

15. The stent loading system of claim 7 wherein the stent includes a therapeutic agent.

16. The stent loading system of claim 1 further comprising a compressed fluid supply, the fluid supply communicating with a solenoid valve which is capable of governing the release of multiple streams of fluid into the contracting aperture.

17. The stent loading system of claim 16 having a fluid accumulator and an accumulator pressurizing pump, the accumulator pressurizing pump further pressurizing and pumping the fluid from the fluid supply into the fluid accumulator, the fluid accumulator in communication with the solenoid valve which governs the release of fluid from the fluid accumulator into the device flow lumen.

18. The stent loading system of claim 16 wherein a fluid dryer is disposed between the compressed fluid supply and the solenoid valve, the fluid dryer drying the fluid from the compressed fluid supply before release into the device flow lumen.

19. The stent loading system of claim 1 wherein the non-contaminating barrier is a polymer sleeve.

20. The stent loading system of claim 19 wherein the sleeve, when in an uninflated condition, is capable of folding and entering into gaps situated between the blades.

21. The stent loading system of claim 17 having a refrigerating chamber, the chamber chilling the fluid within the fluid accumulator.

22. The stent loading system of claim 1, wherein the non-contaminating barrier uses a roll-on/roll-off double spool.

23. The stent loading system of claim 1, wherein the stream of fluid does not transport the non-contaminating barrier outside the contracting aperture device.

* * * * *